(12) United States Patent  
Yang et al.

(10) Patent No.: US 6,670,286 B1  
(45) Date of Patent: Dec. 30, 2003

(54) PHOTOPOLYMERIZATION-BASED FABRICATION OF CHEMICAL SENSING FILMS

(75) Inventors: Xiaoguang Yang, Los Alamos, NM (US); Basil I. Swanson, Los Alamos, NM (US); Xian-Xian Du, Los Alamos, NM (US)

(73) Assignee: The Regents of the University of California, Oakland, CA (US)

( * ) Notice: Subject to any disclaimer, the term of this patent is extended or adjusted under 35 U.S.C. 154(b) by 19 days.

(21) Appl. No.: 10/075,741

(22) Filed: Feb. 13, 2002

(51) Int. Cl.⁷ .................... H01L 21/31; H01L 21/469
(52) U.S. Cl. ................ 438/780; 438/765; 438/795; 427/100; 427/255.18
(58) Field of Search ................. 438/758, 765, 438/780, 782, 795; 427/255.18, 100; 430/311

(56) References Cited

U.S. PATENT DOCUMENTS

| | | | |
|---|---|---|---|
| 4,050,936 A | 9/1977 | Takeda et al. ............... 96/28 |
| 5,151,110 A | 9/1992 | Bein et al. ................... 55/75 |
| 5,326,585 A * | 7/1994 | Nelson et al. ............. 427/163 |
| 5,374,184 A | 12/1994 | Platzer et al. ............. 430/262 |
| 5,397,642 A | 3/1995 | Li et al. .................... 428/403 |
| 5,407,818 A | 4/1995 | von Gentzkow et al. ... 435/180 |
| 5,418,058 A * | 5/1995 | Li et al. .................... 428/327 |
| 5,445,920 A | 8/1995 | Saito ......................... 430/311 |
| 5,468,374 A | 11/1995 | Knoll ........................ 210/96.2 |
| 5,536,783 A | 7/1996 | Olstein et al. ............. 525/129 |
| 5,567,794 A | 10/1996 | Barraud et al. ............. 528/70 |
| 5,792,821 A | 8/1998 | Bowen .................... 526/238.2 |
| 5,910,551 A | 6/1999 | Bowen .................... 526/238.2 |
| 5,929,131 A | 7/1999 | Bowen ....................... 523/116 |
| 6,033,773 A | 3/2000 | Yang et al. ................ 428/333 |
| 6,180,739 B1 | 1/2001 | Bowen .................... 526/238.2 |
| 6,316,268 B1 * | 11/2001 | Yang et al. ................ 436/106 |
| 6,527,961 B1 * | 3/2003 | Vigna et al. ................. 216/2 |

* cited by examiner

*Primary Examiner*—Alexander Ghyka
(74) *Attorney, Agent, or Firm*—Madson & Metcalf

(57) ABSTRACT

A photopolymerization method is disclosed for attaching a chemical microsensor film to an oxide surface including the steps of pretreating the oxide surface to form a functionalized surface, coating the functionalized surface with a prepolymer solution, and polymerizing the prepolymer solution with ultraviolet light to form the chemical microsensor film. The method also allows the formation of molecular imprinted films by photopolymerization. Formation of multilayer sensing films and patterned films is allowed by the use of photomasking techniques to allow patterning of multiple regions of a selected sensing film, or creating a sensor surface containing several films designed to detect different compounds.

41 Claims, 8 Drawing Sheets

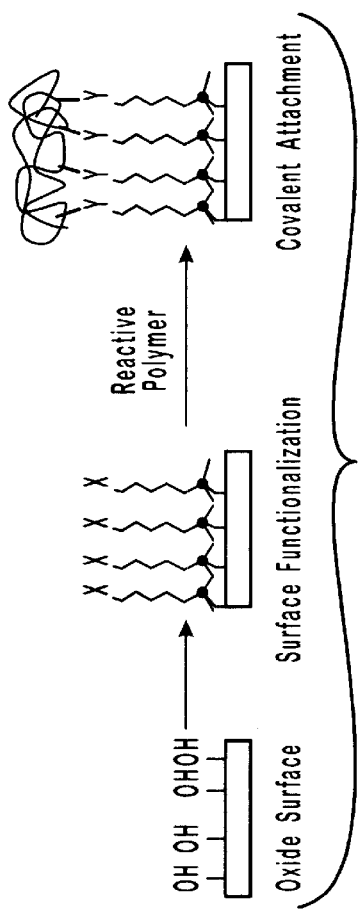
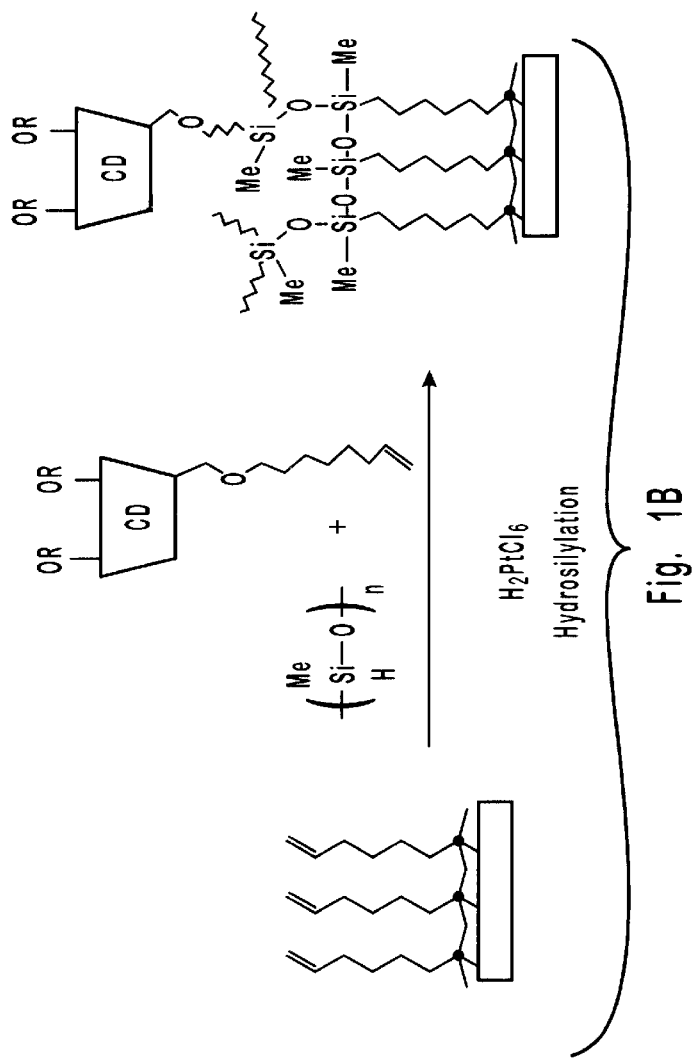
Fig. 1A
Fig. 1B

PHOTOPOLYMERIZATION-BASED FABRICATION OF CHEMICAL SENSING FILMS

GOVERNMENT RIGHTS

This invention was made with Government support under Contract Number W-7405 ENG-36 awarded by the United States Department of Energy to The Regents of the University of California. The Government has certain rights in the invention.

BACKGROUND OF THE INVENTION

1. Field of the Invention

The present invention relates to chemical sensor coatings. More specifically, the present invention relates to processes for covalently attaching and patterning sensing films selectively onto the surface of a sensor using photopolymerization.

2. Description of Related Art

The photopolymerization of acrylates has been intensively studied over a period of decades. *Polym. Int.* 1998, 45, 133; *Mater. Sci. Technol.* 1997, 18, 615. Basic version of the process have been studied and/or patented for various applications, including the UV-curing of acrylate coatings on optical fibers (see U.S. Pat. No. 5,567,794). In addition to these, applications such as imaging processes and information recording (U.S. Pat. Nos. 5,374,184, 4,050,936), photo-resist processes (U.S. Pat. No. 3,660,088), polymerizing liquid crystal structures (Langmuir, 1999, 15, 631), and medical applications (*Proc. Natl. Acad. Sci. USA*, 1999, 96, 3104) have been widely studied and published.

Another area of acrylate photopolymerization receiving attention is the manufacturing of chemical sensing films. Chemical sensing film coatings are currently manufactured using a variety of methods, including the direct coating of polymers or molecules onto a sensor surface (Chemtech 1994, 24, 27), molecular self-assembly (Electronics Letter, 1997, 33, 1651), solution chemistry to covalently immobilize polymeric molecules onto the sensor surface (Langmuir 1998, 14, 1505), and poly-electrolyte layer-by-layer deposition (Sensors and Actuators B, 1997, 45, 87). These methods generally result in the deposition of a sensing film layer onto a surface. In practice, however, films deposited using these methods suffer from problems that decrease their usability.

Among these problems is the lack of effective surface bonding of the film with the surface of its substrate. This problem renders many films susceptible to being stripped from the surface by aging, environments, or physical contact with other objects. This is a significant disadvantage since some such physical contact is incidental to normal use of the sensor. Such stripping renders the sensor less sensitive, and thus less useful. In addition to this problem, the phenomenon of polymer dewetting may cause instability in the resulting film and the formation of "islands" of polymer which affect the sensitivity and accuracy of the sensor.

Other problems stem from the tendency of some films to scatter or absorb light. In many transduction-based sensor systems, a film must be very thin and transparent in order to allow proper sensor function. If the film chosen is not sufficiently thin and transparent, light is lost, thus rendering an optical sensor coated by the polymer inefficient and inaccurate in its function.

Solution-grown films demonstrate improved stability over many of the currently-used techniques for thin-film fabrication. Unfortunately, most such solution chemistry methods require several days of deposition for completion. Such lengthy fabrication methods often add inconvenience and expense to the production costs of chemical microsensor films. Further, many sensors are not robust enough to undergo the lengthy processing, thus further reducing the utility of these methods.

In addition to these problems, many applications require sensors capable of distinguishing multiple chemicals. Current sensing approaches embrace this "dog's nose" approach to chemical sensing, but have difficulty providing sensors having a sufficient number of different elements for binding each different target molecule. Many sensors are incapable of this, and would thus be improved if they were able to sense multiple chemicals at once. One of the greatest difficulties is patterning differing films onto the small elements such as those used in miniaturized, multielement devices. Patterning chemically distinct films onto the sensing surfaces of the different sensor elements could confer such ability. Currently, however, such patterned surfaces are very difficult to inexpensively produce with accuracy, thus resulting in expensive sensors when they are successfully produced. It would clearly be an improvement in the art to provide a method for conveniently and simply producing patterned sensing films and sensors with patterned sensing films.

It should also be noted that alternative mechanisms for chemical sensing on a film are needed to broaden the art and give alternatives to users with needs which are novel or unmet by current technology. One technique currently unsuitable for chemical sensing is molecular imprinting. Molecular imprinting is a technique used to produce powders imprinted by a template molecule. These materials are currently primarily used to separate the template from other substances. In one major application, these powders are used to pack chromatographic columns for use in separations. The methods currently known and practiced, however, do not teach thin, substantially transparent, imprinted films that would be suitable for use in sensing microsensor film applications.

Accordingly, a need exists for a photopolymerization method that produces sensing films that are covalently-attached to a selected surface in seconds. A need further exists for a photopolymerization method that produces cross-linking of reagents upon polymerization, thus forming a highly stable film. A need also exists for a photopolymerization method that allows sensors/surfaces to be patterned by coating them with different sensing films. Finally, a need exists for a photopolymerization method that is suitable for the production of a molecular-imprinted film suitable for use as a chemical microsensor. Such methods and devices are presented herein.

SUMMARY OF THE INVENTION

The apparatus and methods of the present invention has been developed in response to the present state of the art, and in particular, in response to the problems and needs in the art that have not yet been fully solved by currently available methods of fabricating sensing films, apparatuses comprising sensing films, and coating solutions for forming sensing films. Thus, it is an overall objective of the present invention to provide such methods, apparatuses, and solutions which exhibit improvements over the current art.

To achieve the foregoing objective, and in accordance with the invention as embodied and broadly described herein in the preferred embodiment, a method for fabricating sensing films is provided. According to one configuration, the method of attaching a chemical microsensor film to an oxide surface may comprise the steps of pretreating the oxide surface to form a functionalized surface, coating the functionalized surface with a prepolymer solution, exposing the prepolymer solution to an analyte for molecular imprinting and polymerizing the prepolymer solution film with ultraviolet light to form the chemical microsensor film. The method may additionally include the step of rinsing away un-polymerized prepolymer solution and also may include the step of repeating the method with a chemically distinct prepolymer solution and/or analyte template.

In the invention, the surface chosen as the substrate for the chemical microsensor film must be an oxide surface. This is so in order to accommodate many different transduction approaches such as surface acoustic wave (or "SAW"), optical waveguides, fiber optics, and electrical transduction (such as indium-tin-oxide, which is conducting). In addition to surfaces originally including an oxide layer, surfaces for use in waveguide applications or other evanescent transduction approaches without a suitable oxide layer could be made suitable for use by attaching an intermediate layer which would have a surface oxide layer. This could be accomplished by applying a thin layer of $SiO_2$ to the surface of the material to provide the needed free hydroxyl groups. This would be useful in applications where higher index waveguiding materials are used as the sensor substrate.

The step of pretreating the oxide surface to form a functionalized surface may comprise treating the oxide surface with a silane compound. This silane compound may be selected from the group consisting of (3-Acryloxypropanyl)trichlorosilane and 7-octenyltrichlorosilane.

The step of coating the functionalized surface with a prepolymer solution may be accomplished using a method selected from the group consisting of spin-coating, spray-coating, and dip-coating.

The prepolymer solution ma y comprise monomers of the intended polymer alone. The prepolymer solution may alternatively comprise segments of the intended polymer alone. In other alternatives, the prepolymer solution comprises both monomers and polymers of the intended polymer. In some of these, the monomer is a cyclodextrin. The cyclodextrin monomer may be selected from the group consisting of 2-Per-(2,4,6-trimethyl)benzoxy-6-per-(12-acrylaminododecanoxy)-gamma-cyclodextrin, 2-Per-(2,4,6-trimethyl)benzoxy-6-per-(12-acrylaminododecanoxy)-alpha-cyclodextrin, and 2-Per-(2,4,6-trimethyl)benzoxy-6-per-(12-acrylaminododecanoxy)-beta-cyclodextrin, and 5-tetrafulvalenylmethoxy-1-pentene.

In other versions of the method of this invention, the monomer is selected from the group consisting of a wide range of host molecules whose specificity for a "guest" or target molecule can be modified and optimized. This family of molecules includes calix-n-arenes, cyclophanes, and cyclodextrins. Such monomers may generally be varied by altering the R sidechain groups located proximally to the site or region where the monomer interacts with the target analyte. Though the instant invention focuses primarily on cyclodextrins (alpha, beta, and gamma with modified functionality on the side of the rims of the bucket-shaped core), similar methods may be practiced with calix-n-arenes, cyclophanes, and other molecules with polymerizable units (e.g. vinyl groups).

As noted above, the prepolymer solution may further comprise template molecules which become releaseably trapped in the final polymer after photopolymerization. After photopolymerization, the template may be removed by methods known in the art, leaving a pit in the surface of the resulting polymer film in the size and shape of the template. As a result, the film becomes attractive to template molecules or those of similar size and/or shape. Thus, either the target analyte or an analog may be used as a template molecule.

A wide variety of template molecules may be suitable for the practice of the invention. The template molecules may first be selected from the group consisting of TNT (trinitrotoluene), TNB (trinitrobenzene), DNT (dinitrotoluene), and TTF (tetrafulvalene). Sensors tuned to identify these target molecules could, for example, be used in the detection of land mines or other similarly-composed land mines. In other applications, organophosphorous molecules including chemical warfare agents such as DMMP would be suitable templates. TTF devices may be included to detect DNT and TNT by forming change transfer complexes. Other suitable organophosphates could include pesticides and insecticides.

Other target molecules suitable for use as templates could include common industrial chemicals such as arenes, chlorinated hydrocarbons, etc. Such sensors would prove useful in environmental sensing of pollutants, as in ground water testing, or for process monitoring in the chemical industry. Additionally, volatile organic compounds are a useful target.

The methods of the invention using template molecules, referred to as "molecular imprinting," may further comprise the step of extracting the template molecules from the chemical microsensor film after the step of polymerizing the prepolymer solution with ultraviolet light to form the chemical microsensor film.

After application of the prepolymer solution to the surface to be patterned with sensing film, a polymer film is formed by exposing the prepolymer solution to radiation. This step of polymerizing this prepolymer coating may be accomplished with ultraviolet light. The length of exposure needed to form the chemical microsensor film may be from about 1 to about 5 minutes in length. Alternatively, this step may be only from about 2 to about 4 minutes in length. In methods of the invention in which this irradiation step is carried out in an inert atmosphere, the irradiation may last longer than five minutes.

The invention of this application also includes devices for sensing a chemical that comprise a chemical microsensor film formed using the methods of the invention. As noted above, such films are formed by pretreating an oxide surface of the apparatus to form a functionalized surface, coating the functionalized surface with a prepolymer solution exposing the prepolymer film to a templating molecule, and polymerizing the prepolymer solution film with ultraviolet light to form the chemical microsensor film. Such devices may include surface acoustic wave (SAW) devices, optical waveguide devices, fiber optical devices, and field effect transistors.

The invention also includes methods for selectively attaching, or "patterning" a chemical microsensor film to specific regions of an oxide surface. In some versions, this method comprises the steps of pretreating the oxide surface to form a functionalized surface, coating the functionalized surface with a prepolymer solution, exposing the prepolymer film to a templating molecule corresponding to specific sensing elements on attaching a photomask to the functionalized surface so as to leave the specific regions of the functionalized surface intended for attachment of the microsensor film exposed, and polymerizing the prepolymer solution film on the specific regions with ultraviolet light to form the chemical microsensor film. The prepolymer film that has not been exposed to radiation can then be washed away so that the process may be repeated with a different prepolymer solution and a different templating molecule to coat another sensing element. In this manner, multiple sensing elements, each with a different film having distinct recognition, binding properties, can be produced.

The invention further includes apparatuses for sensing a chemical comprising a chemical microsensor film formed using the methods of this invention. This includes apparatus including a chemical microsensor film formed by pretreating an oxide surface of the apparatus to form a functionalized surface, coating the functionalized surface with a prepolymer solution, exposing the preoplymer film to a templating molecule, attaching a photomask to the functionalized surface so as to leave specific regions of the functionalized surface intended for attachment of the chemical microsensor film exposed, and polymerizing the prepolymer solution film with ultraviolet light to form the chemical microsensor film. The apparatus of the invention may be selected from the group consisting of surface acoustic wave (SAW) devices, optical waveguide devices, fiber optical devices, and field effect transistors. Indeed, the method of patterning chemical sensing films taught in the invention is general, being applicable to all transduction approaches, of which optical planar waveguide technology is only an example.

Additionally, the invention includes apparatuses for sensing a chemical that comprise a patterned chemical microsensor film formed by pretreating an oxide surface of the apparatus to form a functionalized surface, coating the functionalized surface with a prepolymer solution, exposing the resulting prepolymer film to a templace molecule, polymerizing the prepolymer solution film or portions thereof left exposed by a photomask with ultraviolet light to form a first layer of chemical microsensor film, and forming the patterned chemical microsensor film by attaching additional layers of chemical microsensor film to regions of the oxide surface by successively repeating the previous steps. These apparatuses may be selected from the group consisting of surface acoustic wave (SAW) devices, optical waveguide devices, fiber optical devices, and field effect transistors.

The foregoing methods of the invention allow for the fabrication of covalently-attached sensing films in brief periods of time. This causes significant reductions in production costs. The methods further allow the chemical cross-linking of the polymerization reagents with the substrate surface, thus yielding a stable film, and as a result, more durable, accurate sensing surface. Further, the method allows for the fabrication of surfaces/sensor array elements with surfaces patterned with multiple types of durable, covalently-bonded sensing films for detecting multiple analytes with the same sensor element. This is accomplished by allowing the elements to be coated with different sensing films. Specifically, the method employs the process of photopolymerization to fabricate sensing films that contain molecular recognition elements and/or polymer cavities for the shape recognition of analytes in the case of molecular imprinting polymer films. Additionally, the method of the instant invention allows the fabrication of elements with multiple sensing films. Finally, the photopolymerization step of the method of the instant invention functions without the use of a photoinitiator, and results in a film that is covalently bonded to the intended surface, and which may, in many cases, be safely cleaned with a variety of organic solvents.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 1A and 1B are schematic diagrams of surface functionalization reaction and the subsequent polymerization of the prepolymer film and the templating molecule to form a sensing film. The steps shown in FIG. 1B can be repeated to cast different sensing elements with chemically distinct filming to produce a multielement sensor array.

DETAILED DESCRIPTION OF THE PREFERRED EMBODIMENTS

The presently preferred embodiments of the present invention will be best understood by reference to the drawings. It will be readily understood that the components of the present invention, as generally described and illustrated in the figures herein, could be arranged and designed in a wide variety of different configurations. Thus, the following more detailed description of the apparatus, system, and method of the present invention, as represented in FIGS. 1 through 8, is not intended to limit the scope of the invention, as claimed, but is merely representative of presently preferred embodiments of the invention.

FIGS. 1A and 1B are graphical representations of the method of fabricating covalently attached sensing films of the instant invention. Sensing films are films that are capable of binding, capturing, or forming a complex with a specific compound. The interaction between the compound and the film is generally based on size selectivity and non-covalent interactions (e.g., van der Waals interactions). Thus, the material of the film must have cavities wherein selective capture or binding of specifically-sized and/or specifically-shaped compounds can occur. This property of the films makes the detection of their target analytes possible by enabling detection of the mass change resulting from the binding of the compound to the film.

In FIG. 1A, an oxide surface showing free hydroxyl groups is first shown. This surface is shown to first undergo a process of surface functionalization. Next, exposure to a reactive polymer causes the formation of a covalently-attached polymeric film. FIG. 1B focuses in on the polymerization step, beginning with a functionalized surface, here showing that each hydroxyl group has been functionalized, now terminating in a vinyl group. In the method of polymerization shown, irradiation results in polymerization of the film only in regions left exposed by the mask.

Figure 2:
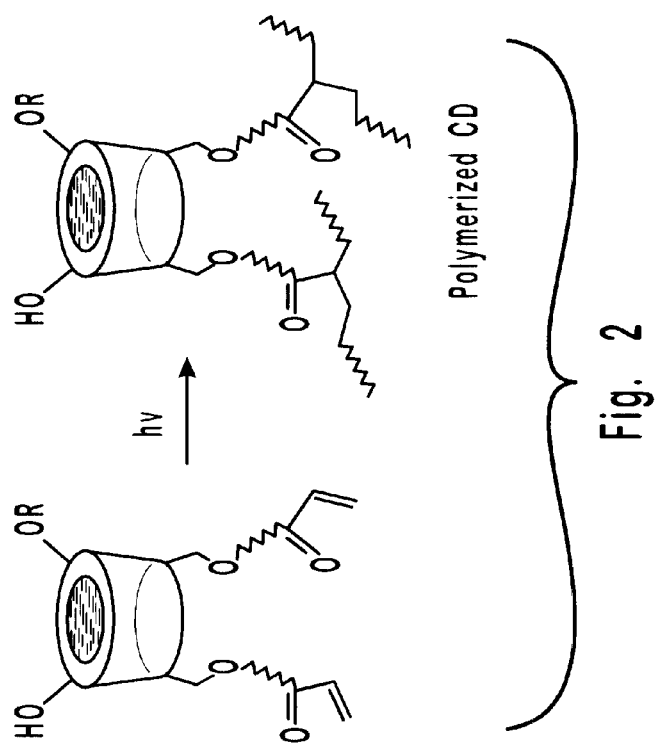
FIG. 2 is a graphical representation of the method of fabricating covalently attached sensing films of the instant invention, focusing on the structural changes undergone by the cyclodextrins used as monomers.

Referring now to FIG. 2, a structural diagram of the polymerization reaction of the instant invention is shown. In this reaction, a modified cyclodextrin is shown partially schematically and partially structurally in its monomer state, and then as a polymer following exposure to ultraviolet light. The cyclodextrin is here represented as having its characteristic "bucket" shape, and to additionally include a free hydroxyl group on the lip of the bucket as well as an R functional group attached to another side of the bucket. In the family of methods of this invention that involves cyclodextrins, the cyclodextrins are selected from the group consisting of 1-per-(2,4,6-trimethyl)benzoxy-6-per-(12-acrylaminododecanoxy)-alpha cyclodextrin, 1-per-(2,4,6-trimethyl)benzoxy-6-per-(12-acrylaminododecanoxy)-beta cyclodextrin, and 1-per-(2,4,6-trimethyl)benzoxy-6-per-(12-acrylaminododecanoxy)-gamma cyclodextrin. In some methods of the invention, segments of previously-polymerized cyclodextrins are used. These segments may similarly be composed of 1-per-(2,4,6-trimethyl)benzoxy-6-per-(12-acrylaminododecanoxy)-alpha cyclodextrin, 1-per-(2,4,6-trimethyl)benzoxy-6-per-(12-acrylaminododecanoxy)-beta cyclodextrin, and 1-per-(2,4,6-trimethyl)benzoxy-6-per-(12-acrylaminododecanoxy)-gamma cyclodextrin.

Many possible functional groups R, as shown in FIG. 2, may be attached to the cyclodextrins of the invention to modulate the size and shape of the bucket section of the cyclodextrin and to thus vary the possible size and configuration of the target analyte. Such functional groups could include hydroxyl groups, amino groups, phosphine groups, and silane groups, as well as substituted amino groups having alkyl substitutions, nitrogen-containing heterocyclic molecules such as a pyridine or imidazole, or may be ethylene diamine. In addition, metal complexes such as lanthanide complexes could be attached to the cyclodextrins for enhanced chemical binding or bonding with chemical warfare agents.

Figure 3:
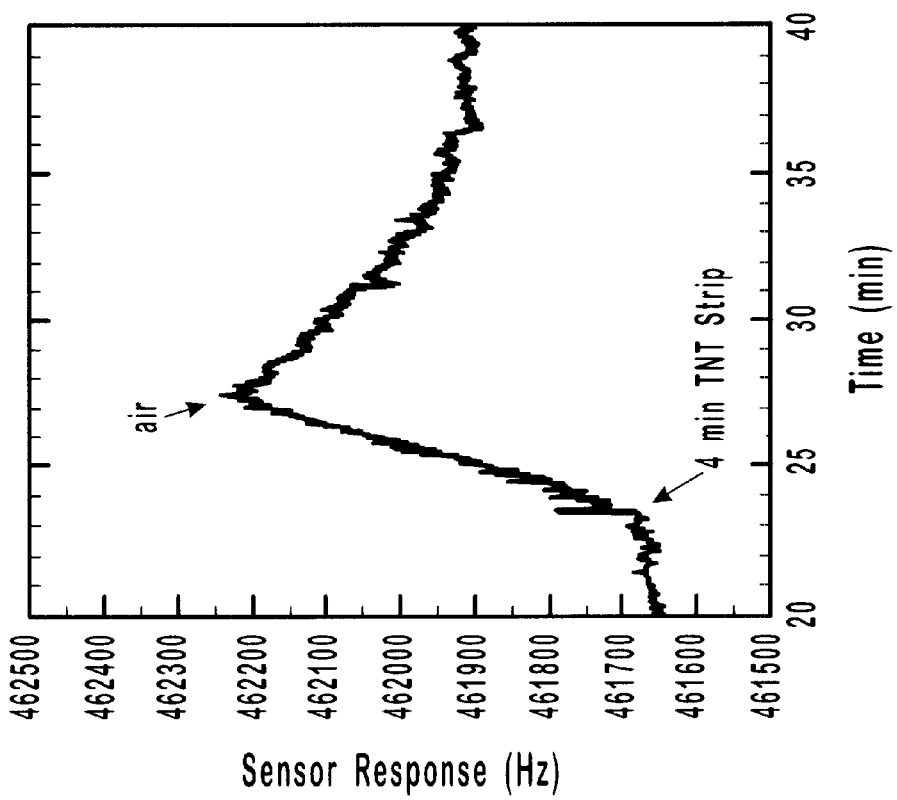
FIG. 3 is a graph showing the response of a SAW sensor of the invention to TNT.
Figure 4:
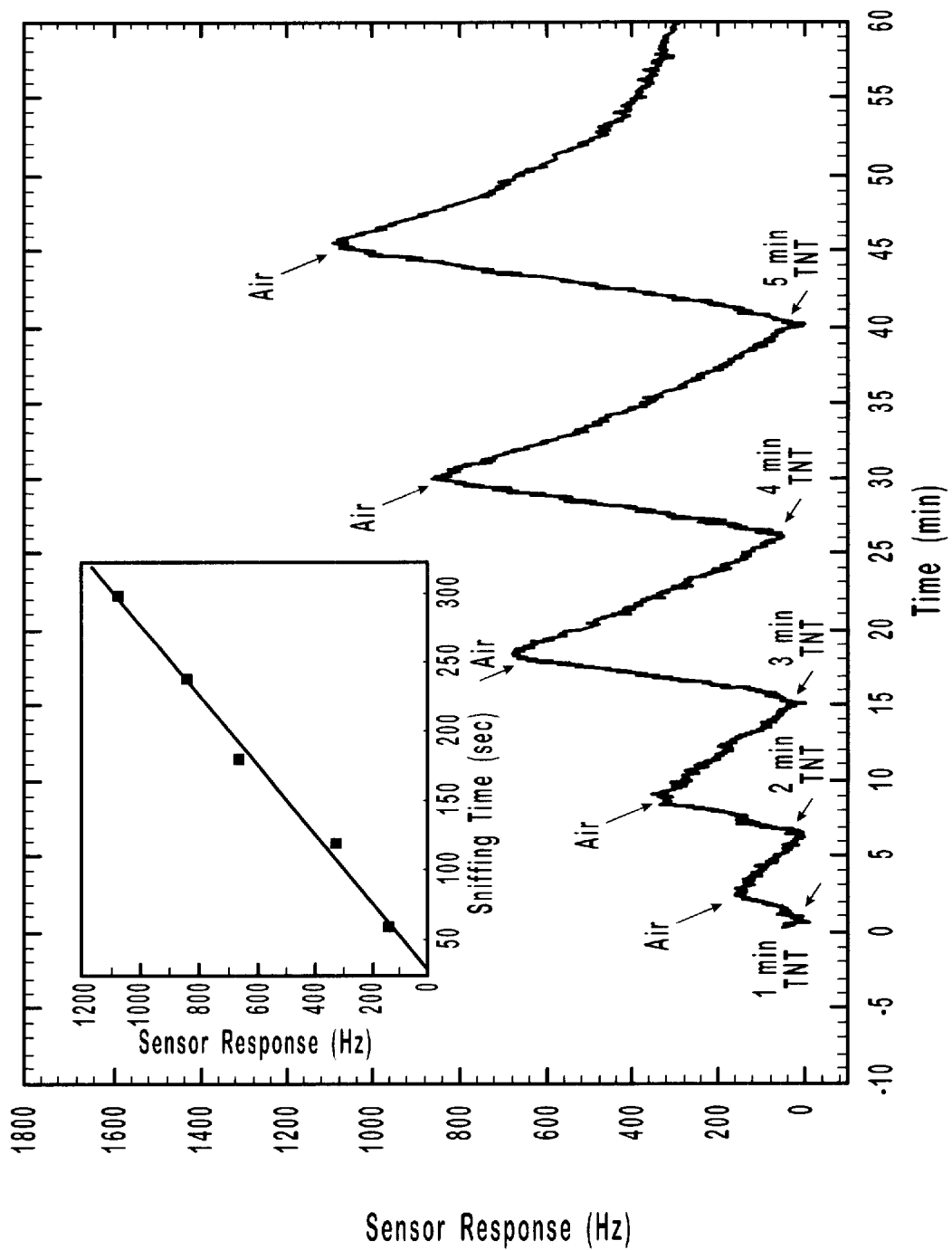
FIG. 4 is a graph showing the response of a SAW sensor of the invention interchangeably exposed to air and to TNT strips.

FIGS. 3 through 8 are graphs showing the response of polymerized sensing films of the invention to exposure to various analytes under varying conditions. Specifically, FIG. 3 is a graph demonstrating the response of a sensor of the instant invention to TNT. The graph demonstrates the response of a microsensor film comprising 1-per-(2,4,6-trimethyl)benzoxy-6-per-(12-acrylaminododecanoxy)-alpha cyclodextrin exposed to TNT for 4 minutes, and then monitored through a total of 20 minutes. FIG. 4 portrays graphically the response of a sensor of the invention which was interchangeably exposed to air and to TNT strips. This figure shows how the magnitude of the sensor response, here measured in Hz, varies in a manner dependent approximately linearly upon the length of the analyte exposure to the sensor.

Figure 5:
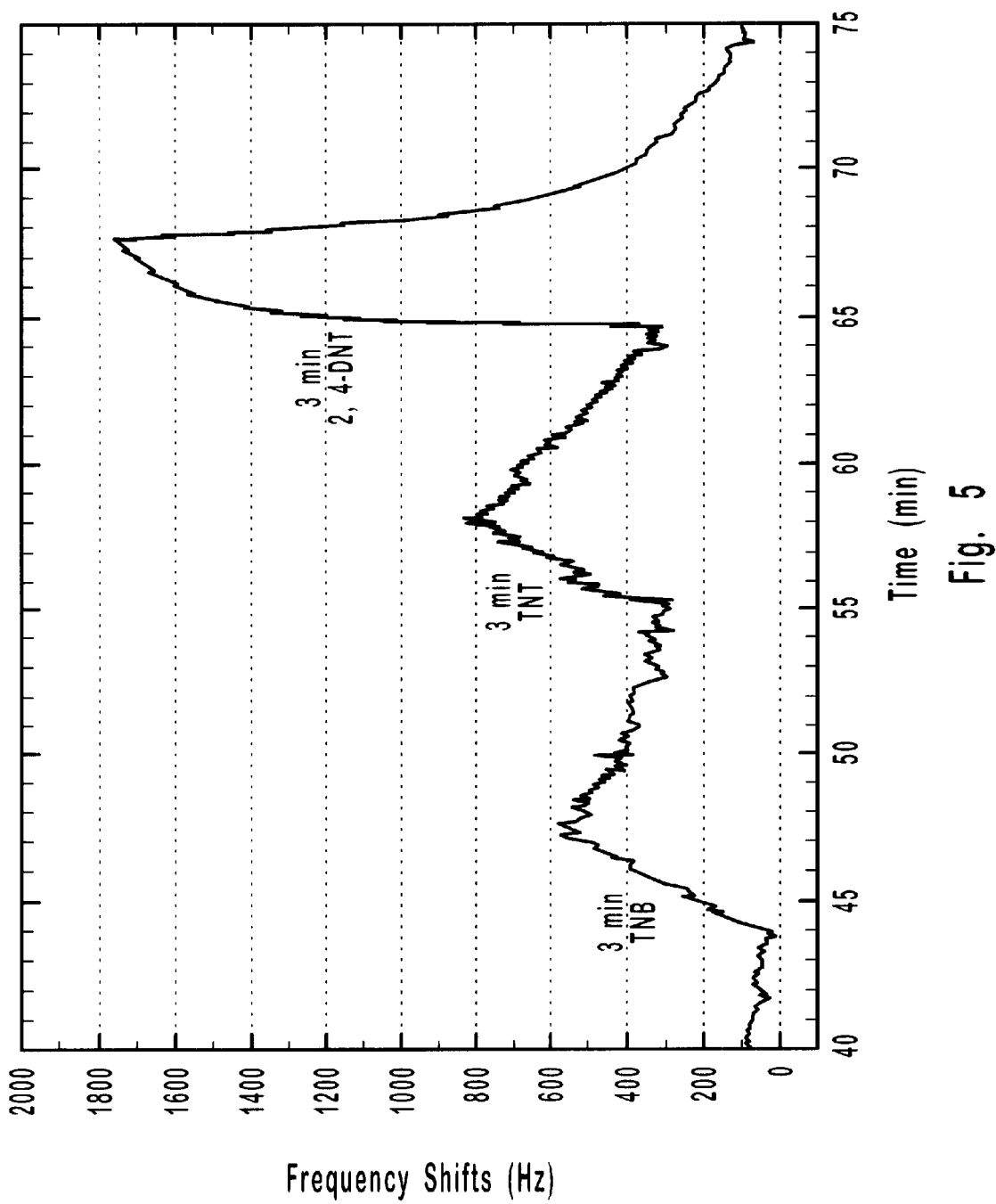
FIG. 5 is a graph showing the response of a SAW sensor of the invention to 1,3,5-trinitrobenzene (TNB), 2,4,6-trinitrotoluene (TNT), and 2,4-dinitrotoluene (DNT) at ambient conditions.
Figure 6:
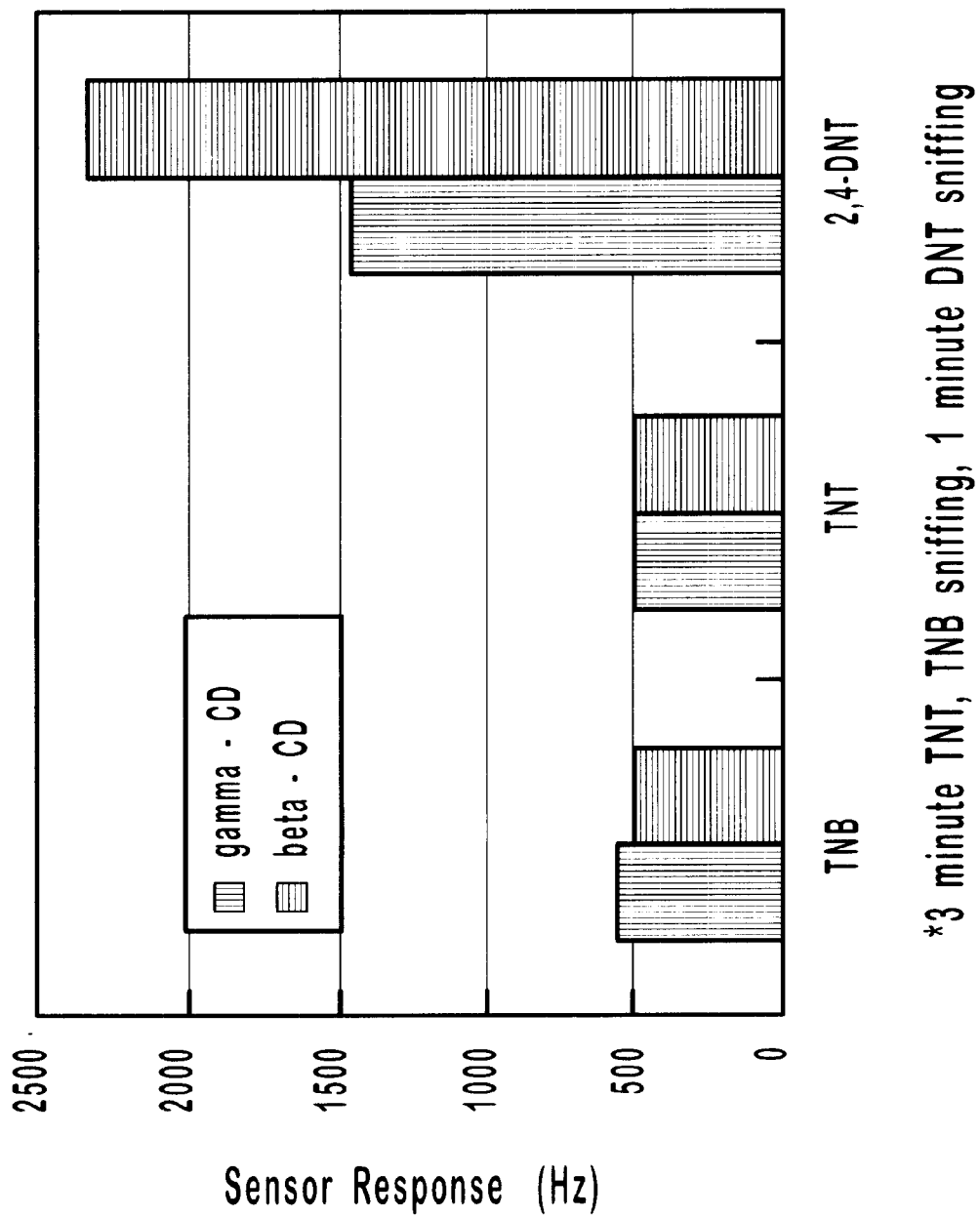
FIG. 6 is a graph showing the selectivity of films made using the methods of the invention using gamma cyclodextrin or beta cyclodextrin toward explosives such as TNB, TNT, and 2,4-DNT.
Figure 7:
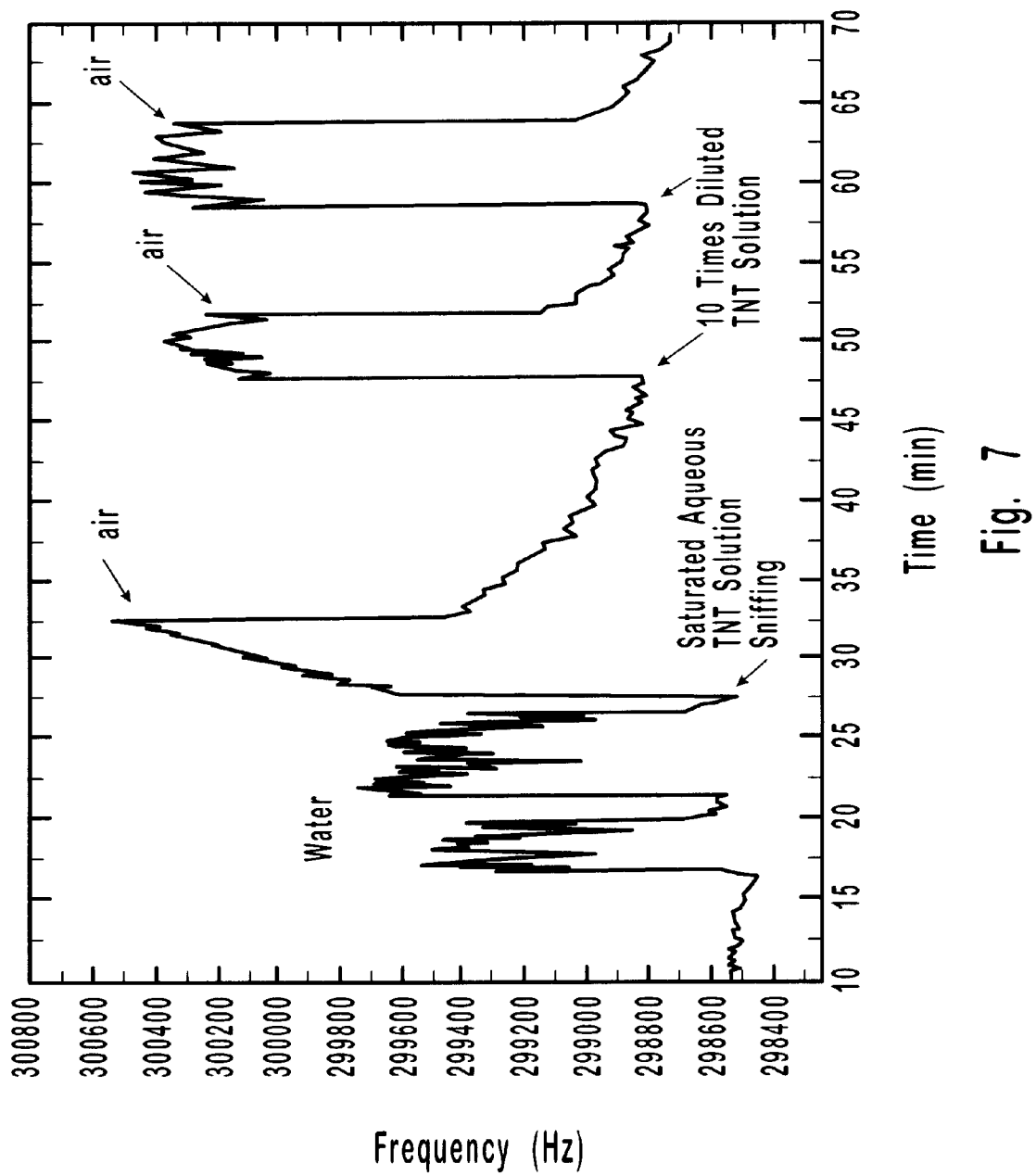
FIG. 7 is a graph showing the response of a sensor of the invention to saturated aqueous TNT solution, interspersed with exposures to air.
Figure 8:
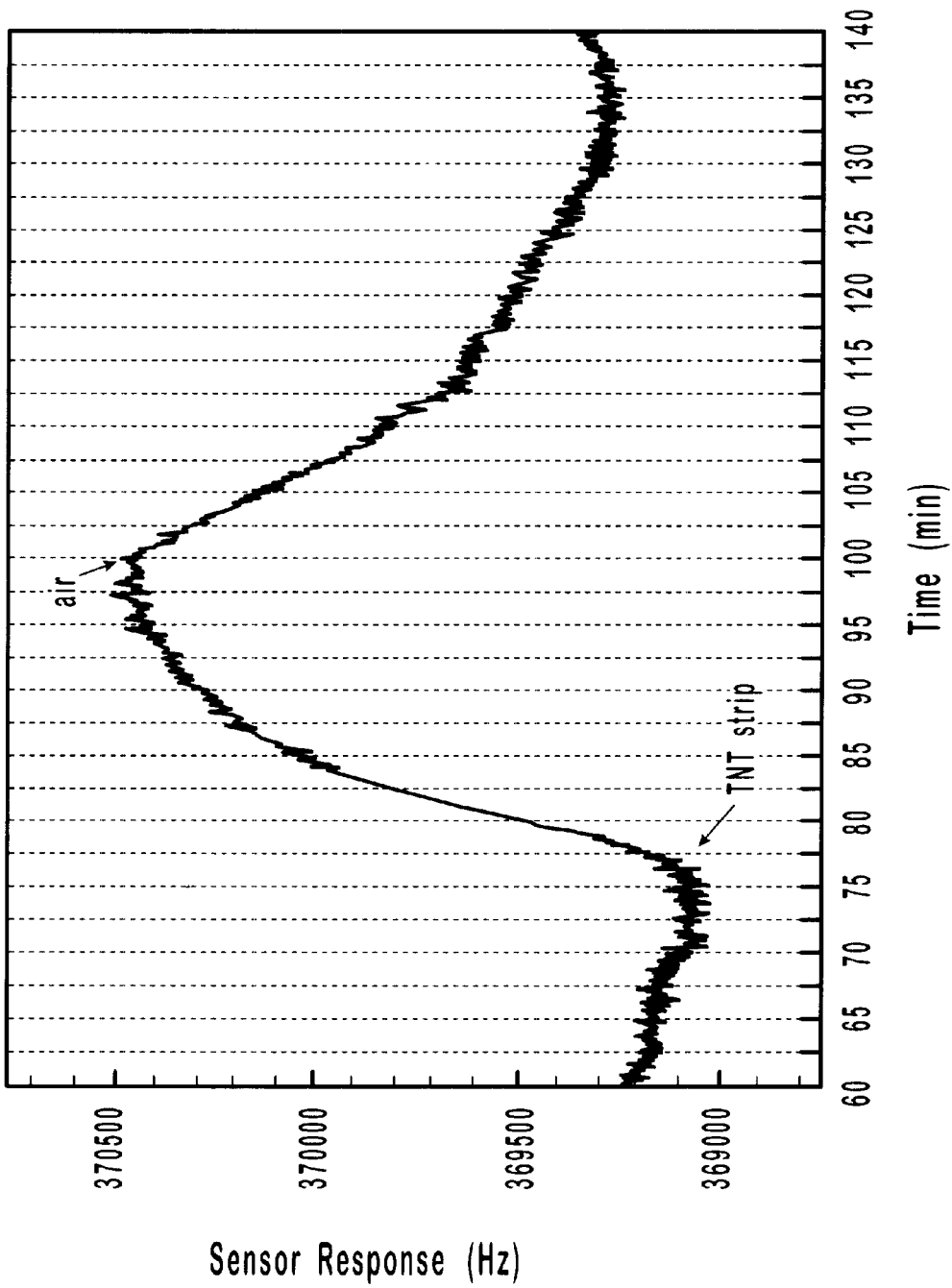
FIG. 8 is a graph demonstrating the saturation of a sensing film of the invention by TNT.

FIG. 5 is a graph showing the response of a sensor of the invention to 1,3,5-trinitrobenzene (TNB), 2,4,6-trinitrotoluene (TNT), and 2,4-dinitrotoluene (DNT) at ambient conditions. This graph shows the varying sensitivity of the specific film used to the TNB, TNT, and DNT; specifically that the sensor is preferential to DNT. FIG. 6 is a graph showing the selectivity of cyclodextrin films of the invention made of different cyclodextrins toward explosives such as TNB, TNT, and 2,4-DNT. This figure shows the differences in analyte selectivity caused by differences in the monomer used in the films of the invention. FIG. 7 is a graph showing the response of a sensor of the invention to saturated aqueous TNT solution, followed by repeated exposures to air, and then to the aqueous TNT solution. Finally, FIG. 8 is a graph demonstrating the saturation of a sensing film of the invention by TNT.

Figure 9:
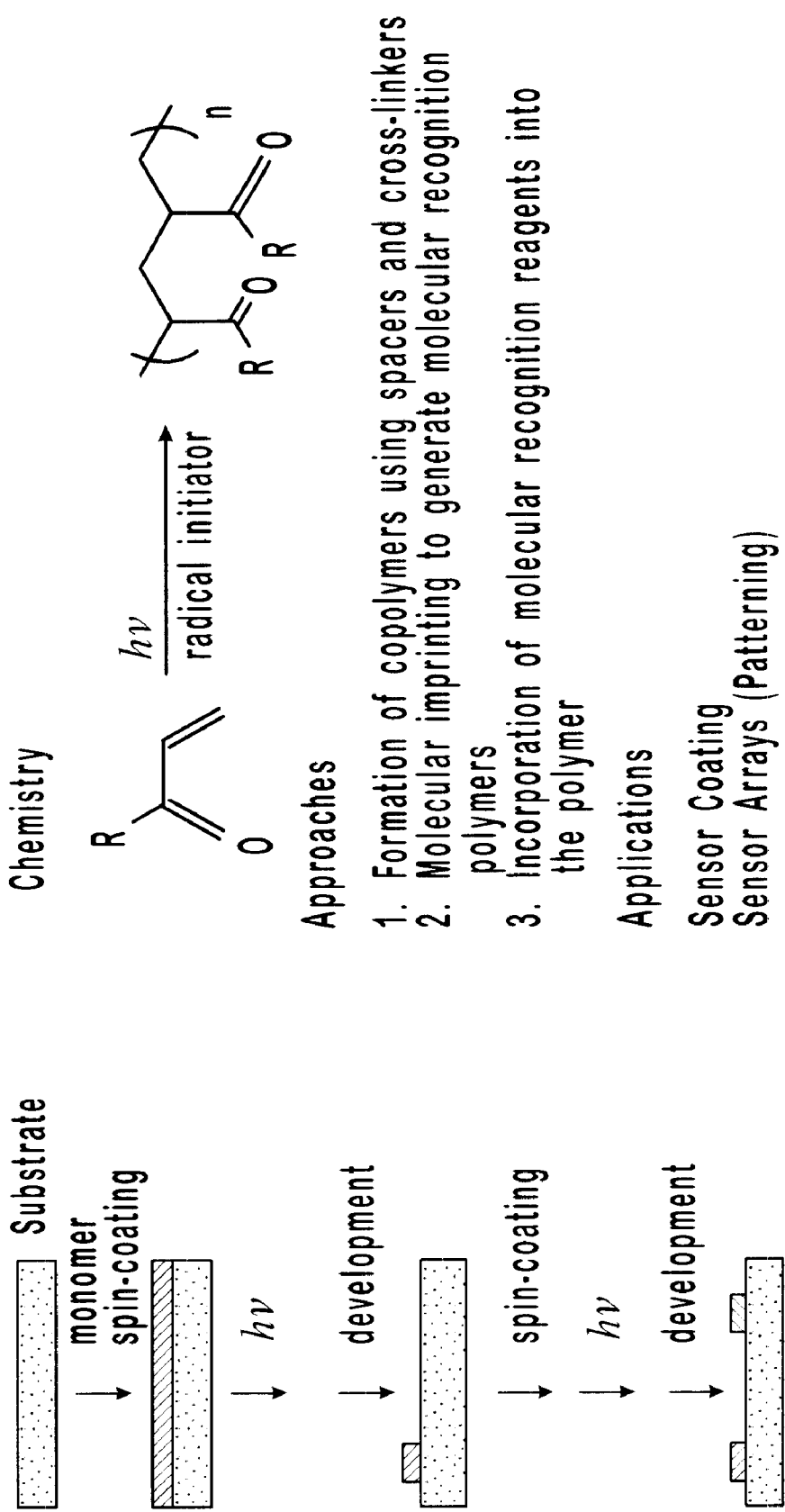
FIG. 9 is a chart graphically demonstrating the method for fabricating a sensor with a patterned chemical sensing film.

FIG. 9 shows graphically the method patterning a sensing film onto a functionalized substrate. First, the substrate is spin-coated with a prepolymer solution that often contains monomers. The resulting prepolymer film is then exposed to a template molecule and irradiated. If the entire surface of the substrate is to be covered in fillm, the entire surface is irradiated. If, however, a patterned film is desired, a photomask is used to permit only the desired region of prepolymer film to be exposed to radiation and thus be polymerized. Following this, the nonpolymerized film may be rinsed away (not shown), and additional rounds of film deposition and photopolymerization may be conducted to yield a patterned film. In this manner, molecular recognition agents are incorporated into stable film which may also be imprinted for additional molecular recognition.

The films of this invention are covalently bonded to a substrate having an oxide surface during the fabrication steps. Many substrates are suitable for use with the method of the invention. The feature which is common to all of them is an oxide surface, as shown schematically in FIG. 1A. Oxide surfaces include those surfaces that exhibit a free surface hydroxyl group, and may thus include substrates such as silicon oxide, silicon, quartz, zinc oxide, zirconium oxide, tin oxide, indium-tin oxide, titanium oxide, lithium niobate, and glass. When the surface to be coated with film is a surface not having surface free hydroxyl groups, in some cases, such as where higher index waveguiding materials are being used, an intermediate layer may be bonded to the surface, the intermediate layer providing the hydroxyl functionalities needed. This may be accomplished by applying a thin coating of $SiO^2$ to the surface.

The sensor devices suitable for the practice of the present invention can include acoustic wave devices and optical transducers. Typically, acoustic wave devices are an arrangement of input and output interdigital transducers formed on a piezoelectric substrate such as quartz or lithium niobate. The input transducer generates an alternating mechanical strain upon application of an alternating voltage field because of the piezoelectric nature of the substrate. The alternating mechanical strain field launches an acoustic wave that if the wave travels along the substrate surface is called a surface acoustic wave (SAW). If instead the wave travels through the bulk of the substrate, it is called an acoustic plate mode (APM). The acoustic wave interacts with a thin film formed on the device surface and is then reconverted into an electrical signal by an output transducer.

The velocity of the wave can be easily determined by operating the device as the feedback element of an oscillator circuit using an RF amplifier. Relative changes in the frequency (f) can be directly related to relative changes in wave velocity (v). In situations where the velocity shift ($\Delta v$) is dominated by changes in the mass density of the film (m, mass/area), these frequency changes ($\Delta f$) can be directly related to the changes in the mass density by:

$$\Delta f/f_o = \Delta v/v_o = -c_m f_o m$$

where cm is a mass sensitivity constant which depends on the piezoelectric substrate and the subscript "o" indicates the unperturbed velocity or frequency.

Identification of species within a liquid or aqueous environment can be better achieved with an APM or Lamb wave device, which are each more effective in liquids than SAW devices which are highly attenuated by liquid contacting the device surface.

Lamb waves propagate through materials of finite thickness. In contrast to a surface acoustic wave, which requires a propagation medium having a thickness on the order of tens to hundreds of times the wavelength of the surface acoustic wave propagating therethrough, Lamb waves require a propagation medium that is at most only several wavelengths in thickness.

Lamb wave sensors generally operate in a frequency range of from about 1 MHz to about 200 MHz, while SAW sensors generally operate in frequency range of from about 10 MHz to about 2,000 MHz. The lower frequency operation of Lamb wave sensors can be more convenient in terms of costs for associated electronic equipment such as frequency counters and feedback amplifiers. Lamb devices re well known and are described in, e.g. U.S. Pat. Nos. 5,212,988, 5,189,914 and 5,129,262.

Suitable optical transducers can be, e.g. a Mach-Zehnder interferometer wherein the cyclodextrin derivative is attached to the oxide surface of one arm of a split waveguide. After formation of any inclusion complexes, a refractive index change would result. The change in refractive index would be measured by a phase shift comparison between the light in the two arms of the interferometer, one arm coated with the selective film and the other arm uncoated, thus allowing for determination and detection of selected chemical species. Generally, use of an optical transducer may allow for a more sensitive detection limit than by use of an acoustic wave device such as a SAW device or Lamb wave device. Moreover, the response of SAW type devices and optical waveguide devices will generally be different for particular chemical species thereby providing complementary information about the identity of the chemical species.

In operation, a surface acoustic wave is launched by applying a rf potential to the source transducers, e.g. source metal interdigital transducers.

Such a SAW resonator device sets up a resonating cavity in operation and such a SAW resonator device is available (without coating) from, e.g. MicroSensors Systems Inc., more specifically a SAW-SR 200A (a 200 MHz on ST quartz). In operation, using both a coated and uncoated resonator device for comparison, a surface acoustic wave is launched by applying a rf potential to the source transducers of the respective resonators, e.g. source metal interdigital transducers. The wave resonators and the wave are then converted back to an electrical signal at the pick up transducers, e.g. pick up metal interdigital transducers. The respective electrical signals are passed through a mixer and a frequency shift is obtained. As the cyclodextrin coating changes in weight due to the inclusion of or chemical binding to either nitro-containing organic compounds or CW agents, the frequency shift will change.

Formation of a chemical separator in the present invention involves securing a cyclodextrin derivative material onto a suitable substrate, e.g. a quartz substrate, having an oxide surface to facilitate chemical bonding through, e.g. a linker agent. The resultant device can function as a chemical separator for nitro-containing organic compounds such as nitrobenzene and the like. After initial formation of the inclusion complex, reversal can be accomplished, e.g. by varying the temperature up to about 60° C. thereby yielding a separation of particular nitro-containing organic compounds from the chemical separator.

Following the provision of an oxide surface suitable for application of a chemical microsensing film, the surface is functionalized with a linker molecule to facilitate the attachment of the polymer. This is generally accomplished by pretreating the oxide surface of the substrate with a solution including a suitable linker molecule. Suitable linker molecules include functionalized silanes. In currently preferred embodiments of the invention, the linkers may be chosen from a group including functionalized silanes such as (3-Acryloxypropanyl)trichlorosilane and 7-octenyltrichlorosilane. Silanes suitable for the invention may, however, be a variety of lengths or sizes. Specifically, useful linking agents can include those of the formula $Br(CH^2)xSi(OR)^3$ where x is an integer from about 6 to about 18, preferably an integer from about 12 to about 18, and more preferably an integer from about 16 to about 18, and where R is selected from among methyl, ethyl, propyl and the like or chlorine. Another class of suitable linking agents includes those having the general formula $Br(CH^2)xSiOH$ where x is an integer from about 6 to about 18, preferably an integer from about 12 to about 18, and more preferably an integer from about 16 to about 18. Yet another class of suitable linking agents includes a alkenylsilanes such as 5-hexenyltrichlorosilane, 7-octenylchlorosilane and the like.

Each such suitable linker includes a terminal vinyl group that may be used to covalently attach the monomer components of the final polymer to the functionalized surface.

In the next generalized step, the functionalized surface is coated with a prepolymer solution in preparation for photopolymerization. This prepolymer solution contains solvents and the components of the final polymer film. In some embodiments of the invention, the only component of the final polymer film included in the prepolymer solution is monomers of the intended polymer. In others, the prepolymer solution includes only segments of the polymer. In still others, the prepolymer solution includes both monomers and segments of the intended polymer.

The monomers and polymers of the prepolymer solution may preferably include cyclodextrin molecules. Cyclodextrins are cyclic molecules made of multiple D-glucopyranose units linked with alpha-(1,4) glycosidic linkages. Three major types of cyclodextrins are known, including α-cyclodextrin, which is made of 6 linked D-glucopyranose units; β-cyclodextrin, which is made of 7 linked D-glucopyranose units; and γ-cyclodextrin, which is made of 8 D-glucopyranose units.

These cyclic molecules are generally bucket-like in shape. The bucket structure of the molecule has hydrophobic inner surfaces and hydrophilic outer surfaces. As a result of this structure, cyclodextrins have the ability of surrounding molecules that are attracted to the hydrophobic inner cavity. As noted above, these molecules are cyclic in shape, and as a result of their differing compositions, have different internal diameters. The 6-unit α-cyclodextrin has a cavity size or internal diameter of about 4.7–5.2 Angstroms (Å), 7-unit β-cyclodextrin has an internal diameter of about 6.0–6.5 Å, and 8-unit γ-cyclodextrin has an internal diameter of about 7.5–8.5 Å. Cyclodextrins may be modified in many ways to modify their functionality. Modified cyclodextrins are referred to as cyclodextrin derivatives. Some examples of useful modifications include adding functional groups by substituting a hydrogen from one of the primary or secondary hydroxyl groups with a carboxyl group, a carboxyl alkyl group, a carboxylaryl group, an alkyl group such as either a lower alkyl ($C_1$ to $C_4$ group) or a longer-chain aliphatic of from about 8 to 22 carbons), a hydroxyalkyl group, a sulfonic group, an amino group, or an alkylenesulfonic group. By attaching such groups, the size of the internal cavity and the binding characteristics of the cyclodextrin may be modified. In some applications, the cyclodextrin may be additionally be modified to include a metal complex ion, such as a lanthanide complex, to aid in binding chemical warfare agents.

In some methods of the invention, the cyclodextrins are chosen from the group of 2-per-(2,4,6-trimethyl)benzoxy-6-per-(12-acrylaminododecanoxy)-alpha cyclodextrin, 2-per-(2,4,6-trimethyl)benzoxy-6-per-(12-acrylaminododecanoxy)-beta cyclodextrin, and 2-per-(2,4,6-trimethyl)benzoxy-6-per-(12-acrylaminododecanoxy)-gamma cyclodextrin.

These monomers and polymers are suitable for use in a sensor due to their ability to interact with molecules such as selected organic compounds including aromatic compounds, e.g., benzene, toluene, xylene and the like, polyaromatic compounds including compounds with fused ring structures containing between about two and ten rings, some or all of which are benzene rings, e.g., naphthalenes, indenes, anthracenes, phenanthrenes, fluorenes, acenaphthenes, benzanthracenes, perylenes, tetracenes, pyrenes, benzopyrenes, benzoperylenes, and the like, oxygen-containing organic compounds, e.g., methanol, acetone, dimethyl sulfoxide, dimethyl forinamide, tetrahydrofuran and the like, and halogenated, e.g., brominated or chlorinated, hydrocarbons, e.g., chloroform, carbon tetrachloride, methylene chloride, trichloroethane, tetrachloroethene, dichloroethylene, trichloroethylene, and the like. It is generally understood that a-cyclodextrin is generally better suited for the inclusion of smaller hydrocarbons, while β-cyclodextrin is generally better suited for the inclusion of larger hydrocarbons, e.g., fused ring compounds such as naphthalenes.

The invention also includes methods for fabricating chemical microsensor films that operate on principles of molecular imprinting. Molecular imprinting is a technology in which a thin film is created with pits in its surface sized to attract and accommodate a target analyte. In these molecular imprinting methods, the polymer solution includes monomers and/or polymers such as cyclodextrins. As above, the monomer may be selected from a group consisting of a wide range of host molecules whose specificity for a "guest" or target molecule can be modified and optimized. This family of molecules includes calix-n-arenes, cyclophanes, and cyclodextrins. Altering the R sidechain groups located proximally to the site or region where the monomer interacts with the target analyte may vary the chemical characteristics of these monomers. Though the instant invention focuses primarily on cyclodextrins (alpha, beta, and gamma with modified functionality on the side of the rims of the bucket-shaped core), similar methods may be practiced with calix-n-arenes, cyclophanes, and other molecules whose core ethylene oxide provides a polymerizable unit.

In the molecular imprinting methods of the invention, the prepolymer solution further comprises a template molecule for imprinting into the final polymer. The product polymer thus also contains these template molecules, which, after photopolymerization, may be removed during an additional removal step. This template removal step could comprise a washing of the surface with a solvent such as an organic solvent. This would leave the polymer surface free of templates, and with an imprinted surface able to attract molecules substantially identical to the substrate molecule used in the fabrication process.

In some presently preferred embodiments of this invention, suitable templates include trinitrotoluene ("TNT"), trinitrobenzene ("TNB"), dinitrotoluene ("DNT"), and TTF (tetrathiafulvalene). A wide variety of template molecules may be suitable for the practice of the invention, however. Sensors tuned to identify these target molecules could, for example, be used in the detection of land mines or other similarly-composed land mines. In other applications, organophosphorous molecules including chemical warfare agents, decomposition products of chemical warfare agents, and precursor materials to chemical warfare agents. In other instances, simulants of chemical warfare agents could be used, such as in circumstances when it is desirable to run a test, but not to have actual chemical warfare agent present for safety reasons. Exemplary simulants include chloroethyl sulfide as a simulant for mustard gas and dimethoxy methyl phosphate as a simulant for sarin (methylphosphonofluoride acid, isopropyl ester) nerve gas. Other suitable organophosphates could include pesticides and insecticides.

Other target molecules suitable for use as templates could include common industrial chemicals such as arenes, chlorinated hydrocarbons, etc. Such sensors would prove useful in environmental sensing of pollutants, as in ground water testing, or for process monitoring in the chemical industry. Additionally, volatile organic compounds are potentially a useful target. Other potential applications of the chemical microsensors of the present invention include use in process monitoring for industrial chemicals, use in toxic organic compound monitoring of gas phases for safety, use in environmental monitoring of storage tank leaks, or use in monitoring of sensitive areas such as airports for restriction of terrorist activities.

Measurements of the frequency responses produced by chemical microsensor, such as with a surface acoustic wave device of the present invention, have shown responses to nitrobenzene of two or three orders of magnitude higher in frequency shift than similar chemical microsensors incorporating the same or other cyclodextrin derivatives engineered for chlorinated hydrocarbons and aromatic organic compounds. As a result of this, detection of nitro-containing organic compounds is possible at levels as low as 10 to 100 ppb of the selected nitro-containing organic compound using a sensor containing a single monolayer of sensing film.

By using only the single monolayer of selected cyclodextrin derivative material film, even lower detection limits of less than 1 ppb may be achieved. Proper selection of the chemical modifications of the cyclodextrin derivative material may control the ultimate sensitivity. Use of multiple layers of cyclodextrin derivative material may also allow for greater sensitivity, i.e. lower detection limits. Measurements of these same target materials (a nitro-containing organic compound such as NB, or nerve gas simulants and mustard gas simulants) against reference films prepared from selfassembled thin films of an alkane ($H_{39}C_{18}SiCl_3$) or perfluorinated alkane ($CF_3(CF_2)_7CH_2SiCl_3$) on a SAW device gives a negligible response. Sensing film thickness can be controlled by adjusting the concentration of the prepolymer solution prior to photopolymerization.

The methods of the invention first include the steps of functionalizing the surface to be coated. FIG. 1B shows the step of attaching the monomer/polymer to the linker molecule. Specifically, FIG. 1B shows the attachment of a functionalized cyclodextrin molecule to the previously-attached linker molecules. The cyclodextrin is shown containing functional groups R on the outer edge of the cyclodextrin "bucket." These functional groups may include a hydrogen substituted from one of the primary or secondary hydroxyl groups with a carboxyl group, a carboxyl alkyl group, a carboxylaryl group, an alkyl group such as either a lower alkyl ($C_1$ to $C_4$ group) or a longer-chain aliphatic of from about 8 to 22 carbons), a hydroxyalkyl group, a sulfonic group, or an alkylenesulfonic group. By attaching such groups, the size of the internal cavity and the binding characteristics of the cyclodextrin may be modified.

The coating step is similarly shared by the methods of the invention. This step may be accomplished by methods including spin-coating, spray-coating, and dip-coating. Spin-coating is a coating process in which the item to be coated is spun, and the coating solution is applied to the item. Optimally, the coating is applied to the center of the item while the item is still spinning. This allows centrifugal forces to pull the coating outward from the center of the item evenly over its surface, thus uniformly coating the item.

Spray-coating is a term that describes a family of processes in which the coating solution is dispensed with some velocity from a sprayer that breaks the solution up into small droplets that contact and adhere to a surface. Some spraying processes additionally utilize electrostatic forces to allow droplets to travel in non-linear paths and adhere to the surface to be coated in order to help assure an even coating.

Finally, dip-coating is a simple process in which the item to be coated is dipped in the coating solution to cover it. As with other coating methods such as those mentioned herein, additional steps may be necessary to remove excess coating material and assure complete coverage of the item or surface. After the prepolymer solution is applied to the surface, the coating may be allowed to dry, thus allowing substantially all of the solvent to evaporate before the photopolymerization step is undertaken.

After the prepolymer solution is applied as a coat over the surface to be patterned with sensing film, the polymer film may additionally undergo molecular imprinting. Following this, the sensing film may be formed by exposing the prepolymer solution to radiation. This photopolymerization step may be accomplished with ultraviolet light. The length of exposure needed to form the chemical microsensor film may be from about 1 to about 5 minutes in length. Alternatively, this step may be only from about 2 to about 4 minutes in length. In inert atmospheres, this step may be longer than 5 minutes.

A synthetic scheme or self-assembly scheme useful in understanding and practicing the photopolymerization step of the present invention can include the following. In a cyclodextrin derivative applied to the surface in a prepolymer solution, a secondary hydroxyl group can be reacted to convert the hydroxyl group to an ester group (OR). R in such an ester group can be an alkyl group, preferably a $C_1$ to $C_4$ alkyl group or substituted $C_1$ to $C_4$ alkyl group, an aryl group such as a phenyl or substituted phenyl, or a sulfonic group and the like. R can also be a carbonyl group such as $R_1$ C(=O)— with $R_1$ being, e.g. hydrogen, an alkyl group such as a $C_1$ to $C_4$ alkyl group or substituted $C_1$ to $C_4$ alkyl group or an aryl group such as a phenyl or substituted phenyl.

Suitable groups for R can include: carboxyl groups wherein $R_1$ is methyl, ethyl, propyl, butyl, hydroxyethyl, hydroxypropyl, benzyl and the like; alkyl groups such as methyl, ethyl, propyl, butyl, hydroxyethyl, hydroxypropyl, benzyl and the like; or, aryl groups such as phenyl and the like. The resultant derivative can be linked to the sensor surface through the linker agent after the linker agent is initially reacted to the oxide surface of the substrate during the functionalization step.

By using these methods, the cyclodextrin cavity can be oriented in a specified position. Reaction with potassium hydroxide and methanol can restore a secondary hydroxyl functionality and the steps can be repeated to build up a multilayer structure with oriented cyclodextrin functionality, as discussed above. Covalent bonding between the cyclodextrin derivative material and the linker material and between the linker material and the substrate surface provides high stability to the resultant chemical microsensor.

Surface properties of the cyclodextrin derivative such as relative hydrophilicity or hydrophobicity can also be chemically tailored. Such tailoring of the properties can change the selectivity and/or strength of chemical binding of the cyclodextrin derivative to the target nitro-containing organic compounds or CW agents.

Multiple repetitions of the polymer deposition and photopolymerization steps may be used to create different types of polymeric structures. These methods may be used to create surfaces with patterned microsensor films. This includes patterning of films only in those areas where a particular sensing film is desired, as well as the patterning of many different films on different regions of the surface to allow the detection of many analytes at a time. This could include the detection of multiple compounds using a single sensor device having a surface patterned with multiple polymers, as well as multiple detections of the same target compound using multiple sensing films for greater accuracy. The methods of this invention used to create these types of films involve the use of a photomask to selectively deposit a film on a desired location, thus leaving other areas free of film for possible later deposition of another film.

As briefly noted above, the methods of the invention may be used to pattern a film over particular regions of a sensor, as well as pattern many varied films over selected regions of the sensor surface. These methods include additional steps associated with using a photomask to protect those portions of the surface not intended for deposition of the film from exposure to ultraviolet radiation, and thus, from polymer film formation. Techniques utilizing photomasks and light to aid in the deposition of materials are often generally referred to as photolithography.

Using these photolithographic methods, a single film may be patterned over many regions of a sensor surface. The surface is assured to be an oxide surface, and then functionalized. Following the functionalization step, the prepolymer solution containing monomers and/or polymers of the intended polymer is applied. Here, prior to photopolymerization, a photomask is attached to the sensor surface so as to protect those regions where a film is not desired from exposure to radiation. Following this, the remaining, unmasked portions are exposed to ultraviolet light. After this photopolymerization step, the reactants remaining unpolymerized may be removed. In this manner, films may be formed on selected portions of the surface of the sensor.

In addition, using these photolithographic methods, sensors may be patterned with multiple sensing films by repeating the steps of applying a prepolymer solution, masking those portions of the sensor where the film should not be formed, and exposing the intended regions to ultraviolet light. Modification of the binding properties of the polymer subunits could also be used to affect how long the interaction between the cyclodextrin or other polymer and the chemical to be sensed would last.

Cyclodextrins are commercially available, e.g. from Sigma Chemical Company, St. Louis, Missouri and from Aldrich Chemical Company, Inc., Milwaukee, Wis.

EXAMPLES

Experimental Materials and Methods

Materials

Benzene, toluene, octane, ethanol, 2-nitrotoluene, 1,12-dibromododecane, sodium hydride, acryloyl chloride, and hydrogenhexachloroplatinate were obtained from Aldrich Chemical Co. (3-Acryloxypropanyl)trichlorosilane and 7-octenyltrichlorosilane were from Gelest, Inc., and used without further purification. ST-cut quartz 250 MHz SAW devices were purchased from Microsensor Systems.

Synthesis of 2-Per-(2,4,6,-trimethyl)benzoxy-6-per-(12-acrylaminododecanoxy)-gamma-cyclodextrins These molecules are obtained by the reaction of acryloyl chloride with 2-per-(2,4,6-trimethyl)benzoxy-6-per-(12-aminododecanoxy) cyclodextrins which are prepared from 2,4,6-trimethylbenzyl chloride reacted with 2-per-sodium cyclodextrins, then treated with sodium hydride and 12-bromododecanyl azide, reduced by sodium borohydride.

Example 1
The Photopolymerization of a SAW Device Surface

A first example of the method of the instant invention is the photopolymerization of the surface of a SAW device. A 250 MHz SAW device was first rinsed with chloroform and was then UV/ozone-cleaned for 15 minutes. The SAW device was next treated with (3-acryloxypropanyl) 7-octenyltrichlorosilane in hexadecane and carbon tetrachloride for 3 hours at room temperature. Following this, the 2-per-(2,4,6-trimethyl)benzoxy-6-per-(12-acrylaminododecanoxy)-gamma-cyclodextrin monomer was coated onto the surface of SAW by dip-coating. The film on the SAW device was then irradiated under UV for 2 to 4 minutes. The SAW device was rinsed with organic solvents and conditioned with various organic solvents for a few hours.

Example 2
The Photopolymerization of an Optical Waveguide Surface

A next example of the invention of this application is the photopolymerization of the surface of an optical waveguide. An optical waveguide was first cleaned with dichloromethane. The waveguide was next treated with (3-acryloxypropanyl)trichlorosilane in a mixture of hexadecane and carbon tetrachloride for 30 to 45 minutes at room temperature. The 2-per-(2,4,6-trimethyl)benzoxy-6-per-(12-acrylaminododecanoxy) cyclodextrin monomer was coated onto the surface of the optical waveguide by spin-coating. The monolayer-coated waveguide was then exposed to a surface polymerization reaction in outline of coating area for 2 minutes under UV lights.

Example 3
SAW Device Sensor Response Test

A next example of the present invention includes testing the response of a SAW device comprising a sensing film of the invention. Vapor streams used for testing the sensor were generated using gravimetrically calibrated bubblers in conjunction with an automated vapor-generation instrument (VG-400, Microsensor Systems). The temperature of the vapor source was controlled at 10.5° C. The flow rate of the vapor stream to the sensor was 100 ml/min. The frequency data was acquired at a resolution of 2 Hz. The sensor responses of a SAW sensor coated with the photopolymerized film (mass loading=486 KHz) to special chemicals is shown in Table 1.

TABLE 1

Photopolymerized SAW Sensor Response Results

| | Response (Hz) |
|---|---|
| Nitrotoluene Concentration (ppb) | |
| 7,964 | 6,750 |
| 1,593 | 1,800 |
| 398.2 | 610 |
| 159.3 | 285 |
| 31.9 | 105 |
| 8.0 | 62 |
| 1.6 | 38 |
| Toluene Concentration (ppm) | |
| 1,699.3 | 7,100 |
| 339.9 | 2,310 |
| 85.0 | 930 |
| 34.0 | 480 |
| 6.8 | 193 |
| 1.7 | 90 |
| 0.3 | 43 |
| Octane Concentration | |
| 785.8 | 1,650 |
| 157.2 | 350 |
| 39.3 | 95 |
| 15.7 | 40 |
| 3.1 | N/A |
| 0.79 | N/A |
| 0.16 | N/A |
| Ethanol Concentration (ppm) | |
| 1,302.4 | 1,000 |
| 260.5 | 170 |
| 39.3 | 80 |
| 15.7 | 50 |
| 3.14 | 30 |
| 0.79 | 20 |
| 0.16 | 15 |
| DMMP Concentration (ppb) | |
| 52,640 | 4,100 |
| 10,528 | 1,410 |
| 2,632 | 530 |
| 1,059 | 280 |
| 210.6 | 98 |
| 52.6 | 40 |
| 10.5 | 20 |

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method of attaching a chemical microsensor film to an oxide surface comprising the steps of:
   pretreating the oxide surface to form a functionalized surface;
   coating the functionalized surface with a prepolymer solution to form a prepolymer solution coating; and
   polymerizing the prepolymer solution coating with light to form the chemical microsensor film.

2. The method of claim 1, further comprising the step of exposing the prepolymer solution coating to a template molecule prior to polymerizing the prepolymer solution coating.

3. The method of claim 2, wherein the template molecule is selected from the group consisting of TNT (trinitrotoluene), TNB (trinitrobenzene), and DNT (dinitrotoluene).

4. The method of claim 1, wherein the step of pretreating the oxide surface to form a functionalized surface comprises treating the oxide surface with a silane compound.

5. The method of claim 4, wherein the silane compound is selected from the group consisting of (3-Acryloxypropanyl)trichlorosilane and 7-octenyltrichlorosilane.

6. The method of claim 1, wherein the step of coating the functionalized surface with a prepolymer solution is accomplished using a method selected from the group consisting of spin-coating, spray-coating, and dip-coating.

7. The method of claim 1, wherein the prepolymer solution comprises monomers.

8. The method of claim 7, wherein the prepolymer solution further comprises polymers.

9. The method of claim 7, wherein the monomer is a cyclodextrin.

10. The method of claim 9, wherein the monomer is selected from the group consisting of 2-Per-(2,4,6-trimethyl)benzoxy-6-per-(12-acrylaminododecanoxy)-gamma-cyclodextrin, 2-Per-(2,4,6-trimethyl)benzoxy-6-per-(12-acrylaminododecanoxy)-alpha-cyclodextrin, 2-Per-(2,4,6-trimethyl)benzoxy-6-per-(12-acrylaminododecanoxy)-beta-cyclodextrin, and 5-tetrafulvalenylmethoxy-1-pentene.

11. The method of claim 7, wherein the monomers are TTF derivative monomers capable of forming charge transfer complexes with DNT or TNT.

12. The method of claim 10, wherein the prepolymer solution further comprises template molecules.

13. The method of claim 12, wherein the template molecules are selected from the group consisting of TNT (trinitrotoluene), TNB (trinitrobenzene), and DNT (dinitrotoluene).

14. The method of claim 12, wherein the method further comprises the step of extracting the template molecules from the chemical microsensor film after the step of polymerizing the prepolymer solution with ultraviolet light to form the chemical microsensor film.

15. The method of claim 1, wherein the step of polymerizing the prepolymer solution with light is accomplished using ultraviolet light.

16. The method of claim 15, wherein the step of polymerizing the prepolymer solution with light to form the chemical microsensor film comprises irradiating the prepolymer solution for between about 1 minute to about 5 minutes.

17. The method of claim 16, wherein the step of polymerizing the prepolymer solution with light to form the chemical microsensor film comprises irradiating the prepolymer solution for between about 2 minutes to about 4 minutes.

18. A method of selectively attaching a chemical microsensor film to specific regions of an oxide surface comprising the steps of:
   pretreating the oxide surface to form a functionalized surface;
   coating the functionalized surface with a prepolymer solution;
   inserting a photomask between the functionalized surface and a light source such that the specific regions of the functionalized surface intended for attachment of the microsensor film remain exposed to the light source;
   polymerizing the prepolymer solution coating on the specific regions with light to form the chemical microsensor film; and
   rinsing the oxide surface with a solvent to remove unreacted prepolymer solution.

19. The method of claim 18, wherein the step of pretreating the oxide surface to form a functionalized surface comprises treating the oxide surface with a silane compound.

20. The method of claim 19, wherein the silane compound is selected from the group consisting of (3-Acryloxypropanyl)trichlorosilane and 7-octenyltrichlorosilane.

21. The method of claim 20, wherein the step of coating the functionalized surface with a prepolymer solution is accomplished using a method selected from the group consisting of spin-coating, spray-coating, and dip-coating.

22. The method of claim 18, wherein the prepolymer solution comprises monomers.

23. The method of claim 22, wherein the prepolymer solution further comprises polymers.

24. The method of claim 22, wherein the monomer is a cyclodextrin.

25. The method of claim 24, wherein the monomer is selected from the group consisting of 2-Per-(2,4,6-trimethyl)benzoxy-6-per-(12-acrylaminododecanoxy)-gamma-cyclodextrin, 2-Per-(2,4,6-trimethyl)benzoxy-6-per-(12-acrylaminododecanoxy)-alpha-cyclodextrin, 2-Per-(2,4,6-trimethyl)benzoxy-6-per-(12-acrylaminododecanoxy)-beta-cyclodextrin, and 5-tetrafulvalenylmethoxy-1-pentene.

26. The method of claim 22, wherein the monomer is a TTF derivative monomer capable of forming charge transfer complexes with DNT or TNT.

27. The method of claim 18, further comprising the step of exposing the prepolymer solution coating to a template molecule prior to the steps of inserting a photomask and polymerizing the prepolymer solution coating.

28. The method of claim 27, wherein the template molecule is selected from the group consisting of TNT (trinitrotoluene), TNB (trinitrobenzene), and DNT dinitrotoluene).

29. The method of claim 27, wherein the method further comprises the step of extracting the template molecules from the chemical microsensor film after the step of polymerizing the prepolymer solution on the specific regions with ultraviolet light to form the chemical microsensor film.

30. A method of attaching a pattern of chemical microsensor films to an oxide surface comprising the steps of:
   pretreating the oxide surface to form a functionalized surface;
   coating the functionalized surface with a prepolymer solution;
   utilizing a photomask such that specific regions of the functionalized surface intended for attachment of a chemical microsensor film remain exposed;

polymerizing the prepolymer solution coating with ultraviolet light to form a chemical microsensor film; and forming the pattern of chemical microsensor films by attaching additional chemical microsensor films to the oxide surface by successively coating the oxide surface with prepolymer solutions, including chemically distinct prepolymer solutions, utilizing a photomask such that specific regions of the functionalized surface intended for attachment of a chemical microsensor film remain exposed, and polymerizing the prepolymer solution with ultraviolet light.

31. The method of claim 30, further comprising the step of exposing the prepolymer solution coating to a template molecule prior to polymerizing the prepolymer solution coating.

32. The method of claim 31, wherein the template molecule is selected from the group consisting of TNT (trinitrotoluene), TNB (trinitrobenzene), and DNT (dinitrotoluene).

33. The method of claim 30, wherein the step of pretreating the oxide surface to form a functionalized surface comprises treating the oxide surface with a silane compound.

34. The method of claim 33 wherein the silane compound is selected from the group consisting of (3-Acryloxypropanyl)trichlorosilane and 7-octenyltrichlorosilane.

35. The method of claim 30, wherein the step of coating the functionalized surface with a prepolymer solution is accomplished using a method selected from the group consisting of spin-coating, spray-coating, and dip-coating.

36. The method of claim 30, wherein the prepolymer solution comprises monomers.

37. The method of claim 36, wherein the prepolymer solution further comprises polymers.

38. The method of claim 37, wherein the monomer is a cyclodextrin.

39. The method of claim 30, wherein the monomer is selected from the group consisting of 2-Per-(2,4,6-trimethyl)benzoxy-6-per-(12-acrylaminododecanoxy)-gamma-cyclodextrin, 2-Per-(2,4,6-trimethyl)benzoxy-6-per-(12-acrylaminododecanoxy)-alpha-cyclodextrin, 2-Per-(2,4,6-trimethyl)benzoxy-6-per-(12-acrylaminododecanoxy)-beta-cyclodextrin, and 5-tetrafulvalenylmethoxy-1-pentene.

40. The method of claim 30, wherein the steps of polymerizing the prepolymer solution with ultraviolet light to form a chemical microsensor film comprises irradiating the prepolymer solution coating for between about 1 to about 5 minutes.

41. The method of claim 40, wherein the steps of polymerizing the prepolymer solution with ultraviolet light to form a chemical microsensor film comprises irradiating the prepolymer solution for between 2 to about 4 minutes in length.

* * * * *